United States Patent [19]
Braatz et al.

[11] Patent Number: 5,091,176
[45] Date of Patent: Feb. 25, 1992

[54] POLYMER-MODIFIED PEPTIDE DRUGS HAVING ENHANCED BIOLOGICAL AND PHARMACOLOGICAL ACTIVITIES

[75] Inventors: James A. Braatz, Beltsville; Aaron H. Heifetz, Columbia, both of Md.

[73] Assignee: W. R. Grace & Co.-Conn., New York, N.Y.

[21] Appl. No.: 510,260

[22] Filed: Apr. 24, 1990

Related U.S. Application Data

[63] Continuation-in-part of Ser. No. 266,445, Nov. 2, 1988, Pat. No. 4,940,737.

[51] Int. Cl.$^5$ .................. A61K 31/74; C07K 3/00; C07G 7/02
[52] U.S. Cl. .................. 424/78.17; 530/402; 530/816; 514/2
[58] Field of Search .................. 530/402, 816; 424/78

[56] References Cited

U.S. PATENT DOCUMENTS

| | | | |
|---|---|---|---|
| 3,939,123 | 2/1976 | Matthews et al. | 260/77.5 |
| 3,959,079 | 5/1976 | Mareschi et al. | 530/402 |
| 4,094,744 | 6/1978 | Hartdegen et al. | 195/63 |
| 4,137,200 | 1/1979 | Wood et al. | 521/159 |
| 4,177,038 | 12/1979 | Biebricher et al. | 8/192 |
| 4,179,337 | 12/1979 | Davis et al. | 435/181 |
| 4,182,827 | 1/1980 | Jones et al. | 528/60 |
| 4,226,935 | 10/1980 | Fusee | 435/14 |
| 4,439,585 | 3/1984 | Gould et al. | 525/127 |
| 4,485,227 | 11/1984 | Fox | 528/61 |
| 4,499,233 | 2/1985 | Tetenbaum et al. | 524/291 |
| 4,569,981 | 2/1986 | Wenzel et al. | 526/67 |
| 4,681,851 | 7/1987 | Baumgarten et al. | 435/262 |
| 4,935,465 | 6/1990 | Gaman | 530/402 |
| 4,946,945 | 8/1990 | Wojdani | 530/402 |

FOREIGN PATENT DOCUMENTS 0247860  5/1987  European Pat. Off.
WO87/00056  1/1987  World Int. Prop. O.

OTHER PUBLICATIONS

J. F. Smith & E. C. Friedrich—"Urethans of 2-Mercaptoethanol"—J. Amer. Chem. Soc.—81/161–62 (1959).
Henri Ulrich et al.—"Base-Catalyzed Reactions of Isocyanates. The Synthesis of 2,4-Dialkylallophanates"—J. Org. Chem.—32/3938–41 (1967).
A. Farkas et al.—"Catalytic Effects in Isocyanate Reactions"—Advan. Catalysis—13/434–39 (1962).
N. V. Katre et al.—"Chemical Modification of Recombinant Interleukin 2 by Polyethylene Glycol Increases its Potency in the Murine Meth A Sarcoma Model"—Proc. NH. Acad. Sci.—84/1487–91 (1987).
A. Abuchowski et al.—"Alteration of Imunological Properties of Bovine Serum Albumin by Covalent Attachment of Polyethylene Glycol*"—J. Biol. Chem.—252/3578–81 (1977).
C. O. Beauchamp et al.—"A New Procedure for the Synthesis of Polyethylene Glycol-Protein Adducts; Effects on Function Receptor Recognition, and Clearance of Superoxide Dismutase, Lactoferrin, and $\alpha_2$—Macroglobulin"—Anal. Biochem.—131/25–33 (1983).
M. J. Knauf et al.—"Relationship of Effective Molecular Size to Systemic Clearance in Rats of Recombinant Interleukin-2 Chemically Modified with Water-Soluble Polymers*"—J. Biol. Chem.—263/15064–70 (1988).

Primary Examiner—Thurman K. Page
Assistant Examiner—Peter F. Kulkosky
Attorney, Agent, or Firm—Vanessa L. Appleby; Jill H. Krafte; Steven T. Trinker

[57] ABSTRACT

Biocompatible polymers derived from isocyanate-capped high molecular weight triols and higher polyols are covalently linked to drugs. These polymer-modified drugs have one or more of the following advantages over the unmodified drug: reduction of immunogenicity of the drug, increased circulating half-life of the drug due to longer residence time in circulation, ability to administer multiple drugs together, and enhanced potency of the drug.

28 Claims, 1 Drawing Sheet

POLYMER-MODIFIED PEPTIDE DRUGS HAVING ENHANCED BIOLOGICAL AND PHARMACOLOGICAL ACTIVITIES

COPENDING APPLICATION

This application is a continuation-in-part of U.S. Pat. application No. 266,445 as filed Nov. 2, 1988 now U.S. Pat. No. 4,940,737.

TECHNICAL FIELD

This invention relates generally to a chemical modification of drugs, particularly peptides, which enhances the biological and pharmacological activity of such drugs. More specifically, this invention relates to covalently binding the drugs to hydrophilic isocyanate end-capped prepolymers. The modification is accomplished by contacting the water soluble prepolymer with a water soluble drug having isocyanate-reactive groups such as, amine (—$NH_2$), sulfhydryl (—SH), hydroxyl (—OH) or carboxyl (—COOH) groups. The polymer-modified drugs are water soluble. The enhanced biological and pharmacological activities of the polymer-modified drugs include increased circulating half-life, decreased immunogenicity and increased potency.

BACKGROUND

The use of drugs for the purpose of producing a particular physiological response is well known in the medicinal arts. Drugs are defined herein as any biologically-active chemical or natural substances useful for treating a medical or veterinary disorder, preventing a medical or veterinary disorder, or regulating the physiology of a human being or animal. There are a number of limitations to the potential therapeutic benefits derived from the clinical use of drugs, including the ability of the drug to elicit an immune response in the circulatory system.

The immune response involves the production of antibodies to the drugs by the circulatory system. This antibody production may decrease or eliminate the desired biological function of the drug, sometimes by causing reduced residence time in the circulatory system (reduced circulatory half-life) or by virtue of the antibody-drug interaction. Circulatory half-life of peptide drugs may also be reduced due to the ability of proteases to readily cleave peptide bonds.

The problems of immunogenicity and short circulatory half-life are well known and various modifications to drugs have been used in attempts to solve them. These include the modification of proteins with substantially straight chain polymers such as polyethylene glycol (PEG) or polypropylene glycol (PPG). There are numerous patents and publications which describe these modification attempts which are represented by Davis et al., U.S. Pat. No. 4,179,337; Katre et al., International Publication No. WO 87/00056, and Katre et al., European Publication No. EP0247860. However, previous modification attempts have used only monofunctional or difunctional polymers. The present invention differs from these prior modifications in that the polymers are trifunctional or greater and that the modification chemistry is through an isocyanate.

U.S. Pat. No. 4,094,744 (Hartdegan) discloses an aqueous solution of protein bound to an isocyanate-capped urethane polymer. However, the Hartdegan solution is prepared under essentially anhydrous conditions and it has been found that chain extension occurs to yield small amounts of insoluble material which is separated by filtration. The preferred methods used to prepare the solution of the present invention are performed under aqueous conditions and do not yield insoluble material. Hartdegan also specifies a linear polyoxyalkylene polyurethane backbone.

The prior art methods of modification do not teach how to use biocompatible isocyanate-capped high molecular weight triols or higher polyols to greatly decrease the immunogenicity of a drug and increase circulating half-life. The present invention offers a unique method of modifying drugs which accomplishes these goals.

SUMMARY OF THE INVENTION

The polymer-modified drugs of this invention have highly desirable properties which make them particularly well suited for use in biological and biomedical applications. The polymer-modified drugs have enhanced biological and pharmacological activities which include reduced immunogenicity of the drug and increased circulating half-life of the drug.

The polymer-modified drugs are prepared by covalently linking biocompatible, hydrophilic isocyanate end-capped prepolymers to drugs through a linkage between the isocyanate (NCO) groups of the polymer and a reactive amine (—$NH_2$), sulfhydryl (—SH), hydroxyl (—OH) or carboxyl (—COOH) group of the drug. In the preferred embodiment, a high proportion of the isocyanate groups are reacted with the NCO-reactive group of the drug yielding individual polymer-modified drugs which are water soluble and which are largely incapable of forming a polymeric structure, although some polymerization may occur. A single polymer molecule may be reacted with more than one drug simultaneously.

It is a particular purpose of this invention to provide polymer-modified drugs which have properties that neither the polymer nor the drug has to any significant extent on its own. The synergistic properties of the polymer-modified drugs include one or more of the following capabilities: reduction of immunogenicity of the drug, increased circulating half-life of the drug, ability to administer multiple drugs together, enhanced potency of the drug due to longer residence time in circulation, and enhanced potency of the conjugated drugs vs. the inconjugated drug due to altered chemistry and/or presentation.

DETAILED DESCRIPTION OF THE INVENTION

Figure 1:
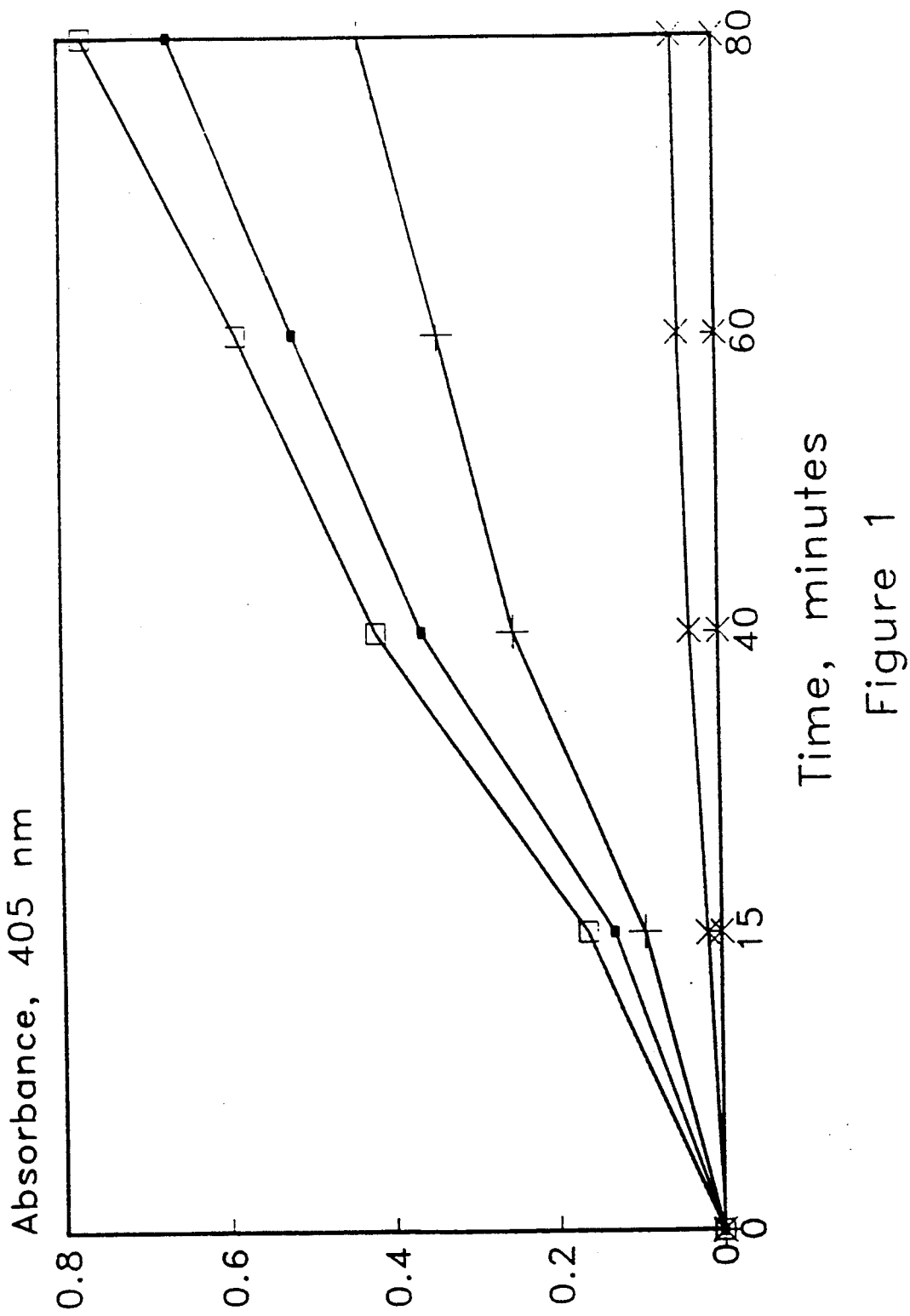
FIG. 1 illustrates the results obtained in an alkaline phosphatase ELISA assay which determined the titers of antisera raised against alkaline phosphatase (#4), alkaline phosphatase covalently coupled to a monofunctional alcohol (#1), alkaline phosphatase covalently coupled to a diol (#2), methanol capped trifunctional polymer (#5) and alkaline phosphatase covalently coupled to a trifunctional polymer of the present invention (#3).

Polymer-modified drugs have been identified which have enhanced biological and pharmacological activities. The prepolymers from which the modified compounds are prepared are isocyanate-capped triols and higher polyols which are made up of at least 75% ethylene oxide monomer units. The polyols have molecular weights of about 7000 to about 30,000 with essentially all of the hydroxyl groups of these triols or higher polyols capped with polyisocyanate, to form the prepolymer. The prepolymer is covalently bound to a drug having an NCO reactive group under conditions which yield a water-soluble product, preferably under aqueous conditions. The NCO-reactive group can be any of a number of groups including amine (—NH$_2$), sulfhydryl (—SH), hydroxyl (—OH), or carboxyl (—COOH) group. The resulting polymer-modified drug is soluble in water and will not form a gel or foam by polymerization through the NCO groups. It is possible that some polymerization could occur by virtue of a drug with multiple NCO-reactive groups binding to multiple prepolymers.

Prepolymer Preparation

The prepolymers used in this invention are isocyanate-capped triols and higher polyols which are made up of at least 75% oxyethylene monomers. The polyols have molecular weights of about 7000 to about 30,000, with essentially all of the hydroxyl groups capped with polyisocyanate. The prepolymers are prepared by reacting the selected triols and higher polyols with polyisocyanate at an isocyanate-to-hydroxyl ratio of about 1.8 to about 2.2 so that essentially all of the hydroxyl groups of the polyols are capped with polyisocyanate. As specific examples of this class of prepolymers, prepolymers from the BIOPOL TM polyurethane prepolymers series available from Grace Specialty Chemicals Co., W. R. Grace & Co.-Conn., will be particularly suitable.

High molecular weight ethylene oxide-based triols and higher polyols are preferably used to prepare the prepolymers and hydrated polymers of the present invention. The polyol molecular weight prior to capping with polyisocyanate should be about 7000 to about 30,000 MW. It is preferred to use trihydroxy compounds (triols) in the preparation of the polyols which are the precursors to the prepolymers and hydrated polymers of this invention. For example, glycerol is a preferred triol. Trimethylolpropane (TMOP), trimethylolethane and triethanolamine are other suitable triols. In addition, tetrols, such as pentaerythritol, may be used to prepare polyols for use in this invention. Triol- or tetrol-based polyols are capped with difunctional or polyfunctional isocyanate compounds as described below to form the prepolymer.

The prepolymers of this invention are formed by reacting the hydroxyl groups of the triols or higher polyols described above with polyisocyanates. "Polyisocyanate" as used herein is intended to refer to both diisocyanates and polyisocyanates, as appropriate, except as indicated by specifying the use of difunctional or polyfunctional isocyanates. Isocyanate end-capped (i.e., isocyanate-terminated) prepolymers are formed. The choice of the polyisocyanate will depend on such factors as biocompatibility of the end product and differential NCO reactivities.

Aliphatic and cycloaliphatic polyisocyanates are preferred for use in this invention, although aromatic polyisocyanates may occasionally be used. Aliphatic polyisocyanates are the most preferred because of decreased toxicological considerations.

Examples of suitable di- and polyfunctional isocyanates are found in the following list.
toluene-2,4-diisocyanate
toluene-2,6-diisocyanate
commercial mixtures of toluene-2,4 and 2,6-diisocyanates
isophorone diisocyanate
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
4,4'-diphenylmethane diisocyanate
3,3'-dichloro-4,4'-biphenylene diisocyanate
1,6-hexamethylene diisocyanate
1,4-tetramethylene diisocyanate
1,10-decamethylene diisocyanate
cumene-2,4-diisocyanate
1,5-napthalene diisocyanate
methylene dicyclohexyl diisocyanate
1,4-cyclohexylene diisocyanate
p-tetramethyl xylylene diisocyanate
p-phenylene diisocyanate
4-methoxy-1,3-phenylene diisocyanate
4-chloro-1,3-phenylene diisocyanate
4-bromo-1,3-phenylene diisocyanate
4-ethoxy-1,3-phenylene diisocyanate
2,4-dimethyl-phenylene diisocyanate
5,6-dimethyl-1,3-phenylene diisocyanate
2,4-diisocyanatodiphenylether
4,4'-diisocyanatodiphenylether benzidine diisocyanate
4,6-dimethyl-1,3-phenylene diisocyanate
9,10-anthracene diisocyanate
4,4'-diisocyanatodibenzyl
3,3'-dimethyl-4,4'-diisocyanatodiphenyl methane
2,6-dimethyl-4,4'-diisocyanatodiphenyl
2,4-diisocyanatostilbene
3,3-dimethoxy-4,4'-diisocyanatodiphenyl
1,4-anthracenediisocyanate
2,5-fluorenediisocyanate
1,8-naphthalene diisocyanate
2,6-diisocyanatobenzfuran
2,4,6-toluene triisocyanate p',p"-triphenylmethane triisocyanate trifunctional trimer (isocyanurate) of isophorone diisocyanate
trifunctional biuret of hexamethylene diisocyanate
trifunctional trimer (isocyanurate) of hexamethylene diisocyanate
polymeric 4,4'-diphenylmethane diisocyanate Capping of the selected triols or higher polyols with polyisocyanates to form the prepolymers used in this invention is effected using stoichiometric amounts of reactants. The isocyanate-to-hydroxyl group ratio preferably should be between about 1.8 and about 2.2. Higher ratios may be used but are not preferred since they may lead to problems associated with excessive monomer present in the final products. The capping reaction may be by any convenient method or procedure. For example, the reaction may be carried out at about 20° to about 150° C., under dry nitrogen, for about 2 hours to about 14 days, preferably in the absence of a catalyst. The preferred temperature is about 125° C. The reaction is terminated when the isocyanate concentration approaches theoretical values. The time period will be a function of the polyol and the polyisocyanate used and the temperature at which the reaction is conducted. Polymerization occurs much more rapidly when aromatic polyisocyanates are used than with aliphatic polyisocyanates. Similarly, the reaction will be more rapid with increased temperatures.

It is preferred to avoid using an excess of polyisocyanate in preparing the prepolymer. Preferably, an isocyanate-to-hydroxyl group ratio of 2:1 (for example, one diisocyanate molecule per hydroxyl group of the polyol) is used to ensure complete end-capping of the polyol. Complete end-capping eliminates excessively high viscosity in the prepolymer by avoiding undue amounts of chain extension. However, a slight excess of isocyanate, i.e., up to about ten percent can be used.

It is characteristic of the present polymer system that the isocyanate content is very low. This is achieved by employing high molecular weight polyols and by avoiding excessive quantities of isocyanate in the end-capping reaction so that free isocyanate monomers are kept at a minimum. The isocyanate concentration in the prepolymer should be above 0.05 milliequivalents per gram and preferably about 0.1 to about 0.43 milliequivalents per gram, for prepolymers formed from triols or high polyols of about 7000 to 30,000 MW.

The drugs

Drugs are modified by the prepolymers prepared as described above to yield polymer-modified drugs with enhanced biological and pharmacological activities. The drug adds a specific functionality or reactivity to the otherwise nonreactive, biocompatible polymeric compound. The polymer adds added stability/protection to the drug. The polymer and drug act synergistically to create a new molecule with desirable traits that neither has on its own to any significant extent.

Drug is defined herein as any biologically-active chemical or natural substance useful for treating a medical or veterinary disorder, preventing a medical or veterinary disorder, or regulating the physiology of a human being or animal. This definition includes peptides such as proteins and hormones, steroids, glycopeptides, antibiotics, mono-, di- and polysaccharides, proteoglycans, lipids, glycolipids, proteolip2ids, lipoproteins, nucleic acids, amino sugars, amino acids, amine surfactants, diamines and polyamines. Particularly preferred drugs are peptides. Suitable peptides include, but are not limited to, peptides such as GHK, RGD, YIGSR, antibodies and alkaline phosphatase.

The modification which is the basis of this invention takes place by reacting the prepolymer with a drug containing isocyanate-reactive groups to form a covalent attachment. The possible isocyanate-reactive groups are numerous, but the preferred NCO-reactive groups are amino (—NH$_2$), sulfhydryl (—SH), hydroxyl (—OH) or carboxyl (—COOH) groups. The rate and extent of the modification reaction will depend in part on the NCO-reactive group of the drug and in part on the relative molar quantities of the prepolymer and the drug. Where the NCO-reactive group is an amino group contained in a diamine or polyamine compound or is a carboxyl group, a large molar excess of the peptide is used so that substantially all of the isocyanate groups of the prepolymer are modified. A single polymer can have more than one drug coupled to it.

In general, sulfhydryl groups react preferentially and rapidly with the isocyanate ("NCO") groups of the prepolymers, under conditions which cause formation of the thiolate ion (—S—), as described below. The thiolate ion reacts with the isocyanate groups of the prepolymer to provide modified prepolymers containing —NHC(O)S—(thiourethane) linkages, even in the presence of amino, hydroxyl or carboxyl functional groups.

However, isocyanate-capped prepolymers will react substantially faster with sulfhydryl-containing drugs than with the drugs containing the other listed groups only when reacted under conditions in which the thiolate anion (—S$^-$) is formed as the active species. Conversely, under conditions where a sulfhydryl-containing drug will not readily form the thiolate reactive group, the prepolymer modification reaction will proceed very slowly and may not occur to any appreciable extent. That is, the presence of the sulfhydryl group alone is not sufficient for the modification reaction in the absence of suitable conditions to form the thiolate ion. For example, reaction of prepolymer and ethanethiol ($C_2H_5SH$) in acetonitrile solvent will not proceed in the absence of a catalyst to ionize the sulfhydryl group of ethanethiol.

The thiolate anion may be formed catalytically by the addition of an extramolecular catalyst. Suitable catalysts would include base catalysts (preferably a tertiary amine such as triethylamine or N-methyl imidazole) or reducing agents such as sodium borohydride. In certain cases, intramolecular or self-catalysis may occur to cause formation of the thiolate ion.

One example of a drug undergoing intramolecular catalysis is cysteamine, formed by treating cystamine (($NH_2CH_2CH_2$)$_2S_2$) with a reducing agent. Specifically, in the presence of mercaptoethanol or another reducing agent, the disulfide bond of cystamine is reduced to form cysteamine ($NH_2CH_2CH_2SH$) which contains both a free amino and a free sulfhydryl group. The amino and sulfhydryl groups of the cysteamine molecule interact to cause formation of the thiolate ion by intramolecular catalysis. The NCO groups of the prepolymer react preferentially with the thiolate group of the self-catalyzed cysteamine molecule, yielding a prepolymer modified via the thiolate so as to have a free amino group.

Alternatively, cystamine itself can be reacted with the prepolymer prior to reduction of the disulfide bond. In this case, the NCO groups of the prepolymer will react with the free amino groups of the cystamine molecule, the second functional group being blocked by the disulfide bond. Following cystamine modification of the prepolymer, a reducing agent such as mercaptoethanol is added to reduce the disulfide bond, creating the sulfhydryl group.

By contrast, reaction of NCO-capped prepolymers with drugs containing an amino group is relatively slower than reaction with thiolate-containing drugs, although reaction is still quite rapid. The amino-NCO reaction forms modified prepolymers containing —NHC(O)NH— (urea) linkages. Reaction rates between the prepolymer and drugs containing amino groups will vary with pH. Unprotonated amines are preferred for faster reaction rates.

Where diamines or polyamines are used as the drug, they should be employed in large excess quantities in order to cause modification of the prepolymer. By "large excess quantities" is meant greater than a 1:1 molar ratio of —NH$_2$ to —NCO groups, preferably greater than 2:1 and most preferably between about 2.1 and about 5:1. It should be understood that use of small amounts of primary or secondary diamines or polyamines will serve the function of crosslinking the modified prepolymer by reacting with the NCO-groups of multiple prepolymer molecules. However, when used in large excess quantities, the diamines and polyamines do not serve the crosslinking function, since it is unlikely that any polyamine molecule will react with NCO-groups from more than one prepolymer molecule. Rather, the reaction serves to modify the prepolymer in the manner of this invention. Monoamines may be reacted in any desired relative quantity.

Reaction of NCO-capped prepolymers with drugs containing hydroxyl groups is slower still, forming modified prepolymers containing —NHC(O)O— (urethane) linkages. Under conditions where the hydroxyl group is maintained, reaction is quite slow. Examples include methanol, ethanol, ethylene glycol, etc. Methanol will react with the prepolymer to form a modified prepolymer having a methyl group as the second functional group. However, reaction may be very fast where the —O$^{31}$ (alkoxide) ion is formed. For example, methoxide or ethyl alkoxide would be suitable modifying compounds and would be reactive.

Drugs with aliphatic or aromatic carboxyl (—COOH) groups may be used to modify the prepolymers. For example, certain amino-protected amino acids and peptides might be reacted with the prepolymer via the carboxyl group. As another example, 2,2-dithiodiethanoic acid can be used as the drug. However, reaction of the prepolymer NCO groups with a carboxylic acid is very slow. The reaction rate can be accelerated by the addition of a base (e.g., triethylamine, N-methyl imidazole, etc.) to ionize the carboxyl group. The polymer-modified drug will contain anhydride or amide linkages.

As with diamine- or polyamine-drugs, drugs containing carboxyl groups should be employed in large excess quantities in order to modify the prepolymer. By "large excess quantities" is meant greater than a 1:1 molar ratio of —COOH to —NCO groups, preferably greater than 2:1 and most preferably between about 2:1 and about 5:1. When used in these large excess quantities, complete or substantially complete modification of the prepolymer-NCO groups occurs.

A drug which contains one or more NCO-reactive group is capable of reacting with the prepolymer through different NCO-reactive groups. It is envisioned that multiple reactive groups on each drug molecule are involved in the preparation of a polymer-modified drug.

Polymer-Modified Drug Preparation

The reaction between the prepolymer and the drug may be conducted in a variety of ways by manipulating the order of addition (e.g., adding drug to prepolymer versus adding prepolymer to drug) as well as the environment in which the reaction is conducted (i.e., water-miscible versus water-immiscible); however, a water-miscible solvent is preferred. Further, the degree of prepolymer modification may be controlled by the relative molar quantities of the components. The end product in all cases is a water-soluble polymer-modified drug.

Water-miscible solvents such as acetonitrile and alcohols are the preferred environment for dissolution of the prepolymer. Preferred alcohols are methanol, ethanol and most preferred is isopropanol, since it does not react with the isocyanates as quickly as other alcohols. In addition, solvents such as toluene, pyridine, and other aprotic solvents, may be used. The solvent should be dried prior to use, for example, by drying over molecular sieves. If methanol or ethanol are used, great care should be taken to thoroughly dry the solvent and to avoid storage prior to use. The isocyanate of the prepolymer may react with water present in the solvent rather than reacting with the drug. To this extent, the prepolymer will undergo polymerization rather than modification.

Since most drugs will be dissolved in an aqueous solution, it is generally important that the drug be in excess with respect to the polymer in order to effectively compete with the water for reaction with the NCO groups of the polymer. One preferred reaction method is to slowly add the polymer in a water miscible solvent to an aqueous solution of drug or drugs with mixing.

The reaction may also be conducted in water-immiscible solvents provided that the drug can be dissolved and retain activity. In this scenario the modification is allowed to proceed in the water-immiscible solvent, the water-immiscible solvent is evaporated, and then the polymer-modified drug is dissolved in an aqueous solution.

Properties of the Polymer-Modified Drugs

The properties of the polymer-modified drugs described herein are unique and offer significant advantages over existing technologies employing polymer-modification. The use of triols and higher polyols is significantly more effective in reducing the immunogenicity of the drugs they modify than the prior art diols and monofunctional polymers. The additional advantages of using triols and higher polyols include multipoint attachment of modifying polymers to target molecules, increased circulating half-life, and increased potency of drugs.

Administration

The present invention provides compositions containing an effective amount of the polymer-modified drugs of the invention, which may alone serve to provide the therapeutic benefits associated with the drug. Such compositions can also be provided together with physiologically tolerable liquid, gel or solid diluents, adjuvants or excipients.

The dosage level of drug in the composition will depend on the in vivo efficacy data obtained after preclinical testing and will depend mainly on the drug employed and ultimate use. Due to the inherent advantages of the polymer-modified drugs (i.e., increased circulating half-life) it is quite likely that a much smaller dosage can be used as compared to administration and dosage of conventional (non-polymer-modified) drugs.

The compositions of this invention are conventionally administered parenterally, by injection, for example, either subcutaneously or intravenously. Additional formulations which are suitable for other modes of administration include suppositories, intranasal aerosols, and, in come cases, oral formulations. For suppositories, traditional binders and excipients may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and contain 10%-95% of active ingredient, preferably 25%-70%. These oral formulations include formulations designed to protect the peptide until it can be absorbed.

Use

The polymer-modified drugs of the present invention may be used to produce a particular physiological response in a wide variety of prophylactic or disease states or conditions. The polymer-modified drugs can be used wherever use of the drug alone could be contemplated. Particular disease states and conditions include, but are not limited to, metastatic tumors, wound-/burn healing, angiogenesis promoters, and atherosclerosis.

Metastasis is the spread of disease from one part of the body to another unrelated part, as in the transfer of the cells of a malignant tumor by way of the bloodstream or lymphatics. It is believed that metastasis is effected through a cascade mechanism which includes adhesion of tumor cells to endothelium, retraction of the endothelium, matrix degradation of the basement membrane and invasion of the tumor cells into the bloodstream. Intervention at any phase in this cascade could be beneficial to the treatment or prevention of metastatic cancers.

Antimetastatic activity is characterized by the ability of the polymer-modified drug to bind to melanoma cells in vitro using the assay of Tuszynski et al. (*Anal. Bio.* (1990) 184:189-91), and the ability to reduce the size and number of tumor colonies in vivo using the assay of Tuszynski et al. (*Cancer Research* (1987) 47:4130-4133). There are a number of mechanisms by which such antimetastatic activity can be occurring. The polymer-modified drugs can be cytotoxic, or inhibit cell proliferation. As inhibitors of cell proliferation, the compounds can act to 1) inhibit mitogenesis, 2) inhibit angiogenesis, or 3) activate the complement pathway and the associated killer cells. Drugs which are useful in inhibiting tumor cell metastasis include, but are not limited to, peptides containing RGD sequences.

Wound healing encompasses biological activities which promote closure of wounds and can be divided into four essential components: inflammation, angiogenesis, collagen deposition and epithelialization. All four components play a role in the healing of wounds. Wound healing activity is characterized by the ability of the polymer-modified drug compounds to show angiogenic activity, the ability of the compounds to stimulate collagen deposition and DNA synthesis in the in vivo sponge model or the ability of the compounds to improve wound healing or reduce healing time in an in vivo partial or full thickness wound model. Drugs which are peptides containing RGD or GHK sequences are particularly useful in wound healing.

Atherosclerosis is a disease state which is characterized by the deposition of small fatty nodules on the inner walls of the arteries, often accompanied by degeneration of the affected areas. Atherosclerotic activity is characterized by the capacity of the polymer-modified drug compounds to inhibit the development of aortic lesions in rabbits fed a high chloresterol diet.

It is envisioned that the present invention can be used in circumstances where it would be advantageous to have two or more drugs in close proximity for effective action. The modification of two or more drugs by the same prepolymer allows both drugs to be present together at the site of action at a higher local concentration than would be possible if the drugs were given together, but uncoupled.

An illustration of such use is the removal of toxic metals from the plasma of transfusion patients with aluminum or iron overload more efficiently than is currently possible. The current therapy is administration of the chelating agent deferoxamine (DFO). The problem with this therapy is that most of the metal in plasma is bound to proteins, principally ferritin. The protein-bound metal is inaccessible for chelation and is lost only as it reequilibrates with the free plasma form, which leads to a very slow rate of metal removal. A very high dose of DFO (as much as four grams per day) is also required.

Other agents, such as ascorbic acid and pyrimidine derivatives, are believed to aid in the mobilization of inaccessible stores of iron. However, at least in the case of ascorbic acid, administration in combination with DFO therapy has shown substantial cardiac toxicity.

In the present invention, both an iron-releasing agent and an appropriate chelator can be chemically linked to the polymer. This provides that a high concentration of chelator would be at the site of released metal. This leads to increased effective potency of the chelator, thus requiring a lower therapeutic dose. Removal of the final complex can be facilitated with the standard Hemo-Kart TM or Alukart TM charcoal hemoperfusion cartridge (National Medical Care, a division of W. R. Grace & Co.). The iron-releasing agents include, but are not limited to, pyrimidine derivatives which release $Fe^{++}$ from ferritin, such as isouramil, and agents which release $Fe^{+++}$ from ferritin. The chelators include, but are not limited to, ferrozine, which complexes with $Fe^{+++}$ and deferroximine, which complexes with $Fe^{+++}$.

The examples which follow are given for illustrative purposes and are not meant to limit the invention described herein. The following abbreviations have been used throughout in describing the invention:

ABTS—2,2'-Azino-bis (3-ethylbenzthiazoline-6-sulfonic acid)
AP—alkaline phosphatase
$CaCl_2$—calcium chloride
° C.—degrees Centigrade
HPLC—high performance liquid chromatography
IPDI—isophorone diisocyanate
μg—microgram
M—Molar
μCi—microcurie
mg—milligram
min—minute
ml—milliliter
mM—millimolar
MWCO—molecular weight cutoff
NaCl—sodium chloride
NCO—isocyanate
ng—nanogram
nm—nanometer
%—percent
PEG—polyethylene glycol

EXAMPLE I

Preparation of Prepolymer A

A prepolymer was prepared by mixing 848.8 g of deionized and dried polyol BASF 1123 (BASF) with 91.6 g isophorone diisocyanate (IPDI) in a one liter polyethylene bottle at room temperature with mechanical stirring for 30 minutes. Dry nitrogen was purged over the mix and the bottle was sealed with a screw cap and placed in an electric oven at 85° C. After 11 days the reaction was terminated. The product had an isocyanate value of 0.43 meq/g and a viscosity of 62,000 cps at 25° C. This prepolymer was designated Prepolymer A (low temperature) A prepolymer was prepared in the identical manner except that it was incubated in an electric oven for 2 days at 125° C. This prepolymer was designated Prepolymer A (high temperature).

EXAMPLE II

Preparation of Prepolymer B

A prepolymer was formed by mixing 403.0 g deionized and dried TPEG20000 TM (Union Carbide Corp.) with 14.78 g IPDI and 0.21 g Santonox R. TPEG20000 TM is a 20,000 MW triol prepared from 100% homopolymeric ethylene oxide. To this mixture 515.0 ml acetonitrile was added to prevent solidification. The resulting mixture was heated as in Example I for 11 days until an isocyanate content of 0.147 meq/g, corrected for solvent (theoretical=0.145 meq/g) was reached. The prepolymer, designated Prepolymer B, was a liquid at room temperature

EXAMPLE III

Preparation of Prepolymer C

A prepolymer was formed by mixing 1570.0 g deionized and dried BASF 1123 polyol (BASF) with 200.0 g Desmodur W TM methylene bis(cyclohexyl diisocyanate) (Mobay Chemical Corp.). BASF 1123 polyol is a 6800 MW polyether triol comprised of 75% ethylene oxide and 25% propylene oxide. The mixture was heated to 85° C. under dry nitrogen for a period of 2-3 days until an isocyanate level of 0.47 meq/g was reached. The resulting prepolymer was liquid at room temperature and had a viscosity of 63,000 cps at 25° C. This prepolymer was designated Prepolymer C.

EXAMPLE IV

A prepolymer was formed by mixing 300.0 g deionized and dried TPEG10000 TM (Union Carbide Corp.) with 22.0 g IPDI and 0.16 g Santonox R. TPEGl10000 is a 10,000 MW triol prepared from 100% homopolymeric ethylene oxide. The mixture was heated at 70° C. under dry nitrogen as in Example I, until isocyanate values reached 0.36 meq/g (theoretical=0.28 meq/g). This prepolymer, designated Prepolymer D, formed a solid when cooled to room temperature.

EXAMPLE V

Conjugation of Alkaline Phosphatase and Prepolymer A

A constant amount of protein was treated with increasing amount of prepolymer and the residual activity was determined. For comparison with Prepolymer A (high temperature) prepolymers, two other isocyanate prepolymers were used. One is a 550 dalton mono methoxy polyethylene oxide end capped with IPDI; the second is a diol (TAKELACK P-24) of molecular weight 2200 comprising 80% ethylene oxide and 20% propylene oxide, end capped with IPDI. Thus the 3+functionality of Prepolymer A is compared to mono- and di-functional isocyanate derivatives.

Alkaline phosphatase, 10 ml of a 5 mg/ml solution in 0.05 M sodium borate, pH 9.0, was mixed with 1 ml of an acetonitrile solution of each prepolymer at varying concentrations.

After one hour at ambient temperature the residual isocyanate was quenched by addition of 9 ml of 0.5 M TRIS, pH 9.0. The samples were then dialyzed vs. 0.05 M sodium borate, pH 9.0 at 4° C. using 7000 MWCO dialysis tubing. Samples of each were assayed for enzymatic activity then stored frozen.

Table 1 lists the relative amounts of protein amine and polymer isocyanate reacted, and the residual enzymatic activity remaining.

TABLE I
EFFECT OF POLYMER MODIFICATION OF ENZYME ACTIVITY

| Prepolymer Used | Sample Designation | Prepolymer NCO:Protein $NH_2$ | alk phos activity dA/dt | % Remaining |
|---|---|---|---|---|
| None | Control | No addition | 0.1200 | 100.0 |
| Mono-func | A1 | 1.5:1 | 0.0788 | 65.7 |
| Mono-func | A2 | 3.0:1 | 0.0634 | 52.8 |
| Mono-func | A3 | 7.5:1 | 0.0426 | 35.5 |
| Mono-func | A4 | 14.9:1 | 0.0313 | 26.1 |
| Di-func | B1 | 1.4:1 | 0.0720 | 60.0 |
| Di-func | B2 | 2.7:1 | 0.0604 | 50.3 |
| Di-func | B3 | 6.8:1 | 0.0389 | 32.4 |
| Di-func | B4 | 13.7:1 | 0.0316 | 26.3 |
| Tri-func Prepolymer A | C1 | 0.7:1 | 0.0790 | 65.8 |
| Tri-func Prepolymer A | C2 | 1.3:1 | 0.0688 | 57.5 |

EXAMPLE VI

Production of antisera to protein-polymer conjugates

Samples A1, B1, and C1 from Example V were selected for use as immunogens, since they retained comparable levels of enzymatic activity. As controls, native enzyme and Prepolymer A end-capped with methanol were used. Production of polyclonal rabbit antisera to these antigens was performed by Cocalico Biologicals, Inc., in Reamstown, PA according to the following protocol:

| Day | Procedure |
|---|---|
| 0 | Prebleed/Inoculation, 100/μg protein |
| 14 | Boost, 50 μg protein |
| 21 | Boost, 50 μg protein |
| 35 | Test bleed |

The five antigens were:
1) alkaline phosphatase—monofunctional PEG(550)
2) alkaline phosphatase—difunctional PEG
3) alkaline phosphatase—Prepolymer A
4) alkaline phosphatase, and
5) Prepolymer A—methanol capped.

EXAMPLE VIII

Quantitation of antibody titers

Antibody titers in the five rabbit sera from Example VI were determined by ELISA based on the following general procedure:
1) antigen is immobilized in 96-well PVC plates,
2) test antiserum is diluted with phosphate-TWEEN-chicken serum (PTCS) and incubated on the plate for 1 hour,
3) the plate is washed and Biotin-Protein A is added for 1 hour, 4) the plate is washed and glucose oxidase-avidin is added for 15 minutes.

5) the plate is washed and substrate (glucose+peroxidase+ABTS) is added. Absorbance at 405 nm is read at intervals on a plate reader.

When alkaline phosphatase was immobilized on the plate at a concentration of 50 ng/well then tested for binding with each of the five test antisera, the following observations were made a) no binding with any of the pre-inoculation, control sera; b) strong binding with antisera raised against alkaline phosphatase (antiserum #4); c) decreased binding with the alkaline phosphatase-monoPEG antiserum (#1), and even less binding with alkaline phosphatase-difunctional PEG antiserum (#2); d) negligible binding with the alkaline phosphatase-Prepolymer A antiserum (#3); and no binding with antiserum against methanol-capped prepolymer A (#5). These results are presented in FIG. 1.

Further, an additional series of ELISA's were performed with each antiserum tested for binding against each of the five antigens. Thus, 50 ng/well of each antigen was immobilized and tested for binding with each antiserum at dilutions of 1:50, 1:100, 1:500 and 1:1000. In each case, the order of reactivity was AP->AP-monoPEG >Ap-DifuncPEG>AP-Prepolymer A>capped Prepolymer A, confirming the original result.

These data demonstrate that Prepolymer A reduces the immunogenicity of this protein. Further, the data shows a progression of reduction which is related to the functionality of the prepolymer. The use of trifunctional prepolymers for this purpose offers an advantage over mono- or difunctional PEGs as derivatizing agents.

Furthermore, the protection was achieved with half (0.7 vs. 1.4) the reactive isocyanate using trifunctional prepolymers. These observations can be extended to include other reactive groups for coupling polymers to proteins, e.g., active esters formed between polyols and p-nitrophenyl chloroformate.

EXAMPLE IX

Conjugation of Alkaline Phosphatase with Prepolymer A

Alkaline Phosphatase from calf intestine, Type I, was obtained from Sigma. A 5 mg/ml solution was prepared in 0.01 M Tris, pH 8.0, containing 1mM $CaCl_2$. To 0.2 ml of this enzyme solution was added 0.02 ml of a 50% (w/w) solution of Prepolymer A (low temperature) in acetonitrile. After 1 hour at ambient temperature the solution was assayed for residual enzyme activity and injected into an HPLC to evaluate the molecular size of the conjugate. Enzymatic activity determined with p-nitrophenylphosphate as substrate indicated 54% of the activity remained after the reaction. Size analysis was performed by HPLC using a Zorbax GF250 column (DuPont) and a mobile phase consisting of 0.05 M sodium phosphate, pH 7.0, with 0.3 M NaCl at a flow rate of 0.5 ml/min. The molecular weight of the enzyme increased from approximately 130,000 to >600,000 after conjugation.

EXAMPLE X

Partial Conjugation of Alkaline Phosphatase with Prepolymer A

The conjugation reaction was conducted as in Example IX but was immediately terminated by addition of 0.2 ml of 0.5 M Tris, pH 8.7. The HPLC profile indicated that an increase in size was obtained, but that it was not as large as in Example IX. Thus, a molecular weight of approximately 250,000 was obtained which did not change over a period of 17 hours after the reaction, suggesting the reaction had in fact been terminated. Enzymatic activities determined at 19 and 48 hours suggested that 72.3 and 86.8% of the original activity remained, respectively.

EXAMPLE XI

Conjugation of Hemoglobin with Prepolymer B

Bovine hemoglobin (Sigma) was dissolved in 0.05 M sodium phosphate, pH 7.0 containing 0.3 M sodium chloride to give a final concentration of 2 mg/ml. Prepolymer B, as a 50% (w/w) solution in acetonitrile, was mixed with 5 volumes of 0.01 M sodium phosphate pH 7.0. After 10 minutes 0.1 ml of the Prepolymer B solution was mixed with 1 ml of hemoglobin and allowed to stand at ambient temperature for 1.25 hours. The product was analyzed by HPLC on a Zorbax column as in earlier examples. The retention time of the protein was observed to change from 20 minutes (corresponding to native, 64,000 MW hemoglobin) to 14.38 minutes, which is the void volume of the column. Thus the molecular weight increased to >600,000.

EXAMPLE XII

Conjugation of Hemoglobin with Prepolymer A

Bovine hemoglobin (Sigma) was dissolved in 0.01 M sodium phosphate, pH 7.0 to give a final concentration of 10 mg/ml. To 0.2 ml of hemoglobin solution were added 0.8 ml of sodium phosphate buffer and 0.02 ml of a 50% (w/w) solution of Prepolymer A (low temperature) in acetonitrile. At times 0, 1, and 3 hours, 0.1 ml of the reaction mixture was removed and added to 0.1 ml of 0.5 M Tris, pH 8.7 to stop the reaction. The molecular size distribution for each sample was determined by HPLC as in earlier Examples. It was observed that the zero time sample already showed significant formation of high molecular weight aggregates which continued to form until essentially complete after 1 hour. No additional changes were apparent after 1hour. The control, untreated hemoglobin eluted as a sharp peak at 20 minutes. The 1 hour sample consisted of a broad peak from 15 to 20 minutes (detection by absorbance at 410 nm) while at 1 hour the profile consisted of a sharp peak at 14 minutes with a broad trailing shoulder to about 17 minutes.

EXAMPLE XIII

Conjugation of YRGDS with Prepolymer A

A pentapeptide with the sequence tyr-arg-gly-aspser (single letter code YRGDS) was obtained from Bachem Inc. and dissolved in water to give a final concentration of 5 mg/ml. To 0.3 ml of YRGDS solution (1.5 mg or $2.51 \times 10^{-6}$ moles) was added 0.03 ml of a 200 mg/ml isopropanol solution of Prepolymer A (high temperature) (6 mg or $2.4 \times 10^{-6}$ equiv. isocyanate). The solutions were mixed and allowed to stand at ambient temperature for 2.5 hours. At that time 25 μl were injected into the HPLC using conditions described in earlier Examples for protein chromatography. Following absorbance at 210 nm, the free peptide eluted at 24 minutes. The reaction mixture showed significant unreacted pentapeptide (about 50%). The remainder of the peptide eluted as a broad series of peaks with retention times from 14 to 19 minutes. The shape of the profile was identical to those obtained when the polymer was conjugated to other low molecular weight, UV-absorbing molecules. Since the polymer alone had little absorbance in this UV region, the broad peak represented polymer conjugated with pentapeptide.

EXAMPLE XIV

Radioiodination of YRGDS-Prepolymer A Conjugate

The conjugate from Example XIII was passed over a disposable Sephadex G25 column (PD10 from Pharmacia, Inc.) to separate free from polymer-bound peptide. Confirmation of the purity of the conjugate was obtained by HPLC. About 45 µg of conjugate (based on peptide) were radiolabeled with 125-iodine using the well known chloramine-T procedure. Free 125-iodine was separated from radiolabeled conjugate using a PD10 column. Of the original 30 µCi of $Na^{125}I$ used for the iodination, more than 23 µCi were incorporated into the conjugate.

EXAMPLE XV

Determination of the Circulatory Half-Life of YRGDS-Prepolymer A Conjugate

Portions of the radiolabeled YRGDS-Prepolymer A conjugate from Example XIV were injected into the tail veins of C57B1/6 mice. As a control, YRGDS free peptide was radioiodinated by the procedure described in Example XIV and also injected. At various times blood was withdrawn from the animals and the amount of radioiodine remaining in the circulation determined using a gamma counter. A biphasic clearance curve ($\alpha:\beta$) was obtained for both species. For the free peptide, about 75% of the label cleared in one minute ($t_{178}\alpha = 30$ secs.) while the remainder cleared with a half life ($t_{\frac{1}{2}}\beta$) of 2 hours 40 minutes. the labeled conjugate on the other hand also had an initial phase in which about 75% of the label cleared, but over a period of about one hour, with a half-life ($t_{178}\beta$) of 33 minutes. The second phase clearance had a half-life ($t_{\frac{1}{2}}\beta$) of 11 hours 20 minutes. Thus by coupling the peptide to this polymer its clearance rate from the circulation is markedly extended.

EXAMPLE XVI

Conjugation of GRGDSPAC with Prepolymer A

A peptide with a sequence of gly-arg-gly-asp-ser-pro-ala-cys (single letter code GRGDSPAC) was obtained from Peninsula Laboratories, Inc. To 22.1 mg of the peptide (2.9×10 moles) dissolved in 1.0 ml PBS was added dropwise, with mixing, 0.5 ml of isopropanol containing 65 mg of Prepolymer A (2.6×10$^{-5}$ equiv. isocyanate). The solution was allowed to stand 17 hours at ambient temperature (although the reaction was complete within 1hour). Analysis by HPLC using conditions described above indicated about 40% of the peptide became bound to the polymer. To separate the free from bound peptide, the sample was dialyzed against 1 liter of distilled water for 27 hours with 4 changes of dialysis water. Dialysis tubing with a molecular weight cutoff of 6000–8000 (Spectrapor) was used for this purpose. The product was determined to be free of contaminating unreacted peptide by HPLC.

EXAMPLE XVII

Biological Activity of GRGDSPAC-Prepolymer A Conjugate

The biological activity of the conjugate formed in Example XV was determined in an assay which measures inhibition of B16 cell spreading on a plate coated with fibronectin. (For details of the assay see: *J. Cell Biol.*, 99 29-36 (1984), and *J. Cell Physiol.*, 130 21-28 (1987). The unconjugated pentapeptide GRGDS exhibits 50% inhibition of cell spreading at a concentration of 0.34 mM. For the GRGDSPAC-Prepolymer A conjugate, 50% inhibition of binding occurred at 0.34 mM, based on octapeptide. Thus, the peptide fully retained its activity in conjugate form.

EXAMPLE XVIII

Cystamine Modification of Prepolymer A

Excess cystamine was added to insure that all the isocyanates on Prepolymer A (high temperature) were endcapped. Cystamine, 1.5 g, (Aldrich Lot No. 02016cj) was dissolved in 150 mls of 50 mM sodium bicarbonate, pH 8.5. This solution was added to 20 g of Prepolymer A (high temperature) and stirred. A gel did not form, therefore the assumption was made that the fourfold excess cystamine capped all the isocyanate groups, thus preventing crosslinking. While stirring, 0.6 mls of mercaptoethanol was added to the cystamine/prepolymer solution to reduce the cystamine to cysteamine. After dialyzing in deionized water, 55 mM mercaptoethanol solution in PBS was added and the mixture was stirred. The product was filter sterilized through a 0.2 µm filter.

EXAMPLE XIX

Angiogenic Activity Bioassay System

Bovine capillary endothelial cells were plated in Minimal Essential Medium containing 5% fetal bovine serum (FBS). After 18 hours, the adherent cells were washed and incubated in M199 medium containing 2% ultrafiltered FBS plus various concentrations of the conjugate of Example XVIII. After an additional 48 hours, the cell numbers were determined. The results of this assay are shown in Table II.

TABLE II

| | Additions | Cell Number |
|---|---|---|
| Exp. I | | |
| Control | None | 27,460 |
| Conjugate of Ex. XVIII | 6.3 µg/ml | 43,920 |
| | 18.9 µg/ml | 52,740 |
| | 63 µg/ml | 47,800 |
| Exp. II | | |
| Control | None | 4,700 |
| Conjugate of Ex. XVIII | 63 µg/ml | 7,650 |
| | 125 µg/ml | 8,620 |
| | 250 µg/ml | 8,560 |
| | 625 µg/ml | 8,870 |
| | 1250 µg/ml | 10,390 |
| Exp. III | | |
| Control | None | 11,510 |
| Conjugate of Ex. XVIII | 125 µg/ml | 25,440 |
| | 500 µg/ml | 47,930 |
| | 1250 µg/ml | 76,300 |

EXAMPLE XX

Preparation of a Peptide Liver Cell Growth Factor/Prepolymer A Conjugate

Ten milligrams ($2.94 \times 10^{-5}$ moles) of the tripeptide Gly-His-Lys (also known as liver cell growth factor) was dissolved in 0.5 ml of PBS. To this solution was slowly added, with mixing, 0.5 ml of dry 2-propanol containing 62 mg ($2.65 \times 10^{-5}$ eq NCO) of Prepolymer A (high temperature). The solution was kept at room temperature for 17 hours, then dialyzed exhaustively against distilled water to remove unreacted peptide.

EXAMPLE XXI

Enhanced Biological Properties of Polymer Modified Peptide with Growth-Promoting Properties The conjugate of Ex. XX was tested for its ability to promote growth in an assay described by Pickart et al. (*Biochem. Biophys. Res. Comm.* 562–566 (1973)). Human HepG2 hepatoma cells (ATCC) were grown in WRC 935 ® medium (Amicon Division, W. R. Grace & Co.) supplemented with 1% fetal bovine serum. Cells were plated in growth medium at $20 \times 10^3$ cells/dish in the absence or presence of the tripeptide Gly-His-Lys (GHK). After 7 days, cells were removed from dishes by trypsin/EDTA digestion and cell numbers determined by using a Coulter TM particle counter. The results are shown in Table III.

TABLE III

| Sample | Cell Number($\times 10^{-3}$) |
| --- | --- |
| Control (no additions) | 180 |
| 0.03 µg GHK | 177 |
| 0.30 µg GHK | 230 |
| 3.0 µg GHK | 260 |
| 0.03 µg GHK/Prepolymer A conjugate of Ex. XX | 276 |

EXAMPLE XXII

Tyrosine Modification of Prepolymer A

A solution was prepared by dissolving 1.63 g L-tyrosine in 100.0 ml water containing 0.1 ml sodium bicarbonate and adjusting the pH to 11–12. A 5.0 g quantity of Prepolymer A (low temperature) was dissolved in 10.0 ml 2-propanol and added to the tyrosine solution dropwise with stirring. This calculates to be a 5.5-fold excess of tyrosine amino groups over prepolymer NCO groups. The excess tyrosine was removed by dialysis against water.

The dialyzed composition was analyzed by gel filtration chromatography on Sephadex G-25. Tyrosine-modified prepolymer eluted in the excluded volume where the marker blue dextran eluted. Free tyrosine standard eluted at twice that elution volume. The dialyzed composition appeared to be free of free tyrosine by this analysis.

EXAMPLE XXII

Tyramine Modification of Prepolymer A

Prepolymer A (low temperature) (5.09 g, 2.19 meq NCO) was dissolved in 5.0 ml 2-propanol. This solution was added dropwise with stirring to 50.0 ml of 0.05M sodium phosphate (pH 7.0) containing 0.38 g (2.19 mmoles) tyramine hydrochloride (Sigma Chemical Co.). The resulting turbid solution was stirred for 17 hours at room temperature. A 10.0 ml portion of the product was dialyzed against 500.0 ml water for 46 hours with four changes to remove unreacted free tyramine.

What is claimed is:

1. A method for enhancing biological or pharmacological activity of a biologically active peptide comprising preparing an aqueous solution of a liquid polymer-modified version of said peptide by covalently binding said peptide to a biocompatible prepolymer under aqueous conditions, wherein said prepolymer is a triol or higher polyol made up of at least 75% oxyethylene monomers, said polyol having a molecular weight of about 7,000 to about 30,000, said polyol having essentially all of the hydroxyl groups capped with aliphatic or cycloaliphatic polyisocyanates, wherein said covalent bond is between an isocyanate group of said prepolymer and an amino, sulfhydryl, carboxyl or hydroxyl group of said peptide, wherein the amount of chain extended insoluble material is reduced.

2. The method of claim 1 wherein the polymer-modified peptide is less immunogenic than the peptide alone.

3. The method of claim 1 wherein the polymer-modified peptide has a longer circulating half-life than the peptide alone.

4. The method of claim 1 wherein the peptide is selected from the group consisting of alkaline phosphatase, hemoglobin, YIGSR, YRGDS, GRGDSPAC, and GHK.

5. The method of claim 1 wherein more than one peptide is covalently bound to the prepolymer.

6. The method of claim 1 wherein said polyisocyanate is isophorone diisocyanate or methylene bis (cyclohexyl diisocyanate).

7. An improved method of producing a biological or pharmacological response in a human being or animal by administration of a biologically active peptide, the improvement comprising administering an aqueous solution of a liquid polymer-modified version of said peptide prepared by covalently binding said peptide to a biocompatible prepolymer under aqueous conditions, wherein said prepolymer is a triol or higher polyol made up of at least 75% oxyethylene monomers, said polyol having a molecular weight of about 7,000 to about 30,000, said polyol having essentially all of the hydroxyl groups capped with aliphatic or cycloaliphatic polyisocyanates, wherein said covalent bond is between an isocyanate group of said prepolymer and an amino, sulfhydryl, carboxyl or hydroxyl group of said peptide, wherein the amount of chain extended insoluble material is reduced.

8. The method of claim 7 which promotes wound healing.

9. The method of claim 8 wherein said wound is a burn.

10. The method of claim 8 wherein said peptide contains the sequence RGD or GHK.

11. The method of claim 7 which inhibits tumor cell growth and metastasis.

12. The method of claim 11 wherein said peptide contains the sequence RGD.

13. The method of claim 7 which inhibits atherosclerotic activity.

14. The method of claim 7 wherein said polymer-modified peptide is admixed with at least one pharmaceutically acceptable carrier prior to being administered.

15. The method of claim 7 wherein an aqueous solution is administered.

16. The method of claim 7 wherein more than one peptide is covalently bound to the polymer.

17. The method of claim 7 wherein the polymer-modified peptide is less immunogenic than the peptide alone.

18. The method of claim 7 wherein the polymer-modified peptide has a longer circulating half-life than the peptide alone.

19. A method of treating a disease state or condition comprising administration of an aqueous solution of a pharmaceutically active amount of a liquid polymer-modified biologically active peptide, wherein said polymer-modified peptide is prepared by covalently binding said peptide to a biocompatible prepolymer under aqueous conditions, wherein said prepolymer is a triol or higher polyol made up of at least 75% oxyethylene monomers, said polyol having a molecular weight of about 7,000 to about 30,000, said polyol having essentially all of the hydroxyl groups capped with aliphatic or cycloaliphatic polyisocyanates, wherein said covalent bond is between an isocyanate group of said prepolymer and an amino, sulfhydryl, carboxyl or hydroxyl group of said peptide, wherein the amount of chain extended insoluble material is reduced.

20. The method of claim 19 wherein the polymer-modified peptide is less immunogenic than the peptide alone.

21. The method of claim 17 wherein the polymer-modified peptide has a longer circulating half-life than the peptide alone.

22. The method of claim 19 which promotes wound healing.

23. The method of claim 22 wherein said wound is a burn.

24. The method of claim 19 which inhibits tumor cell growth and metastasis.

25. The method of claim 19 which inhibits artherosclerotic activity.

26. The method of claim 19 wherein said polymer-modified peptide is admixed with at least one pharmaceutically acceptable carrier prior to being administered.

27. The method of claim 19 wherein an aqueous solution is administered.

28. The method of claim 19 wherein more than one peptide is covalently bound to the polymer.

* * * * *